United States Patent [19]

Yamada et al.

[11] Patent Number: 5,306,627
[45] Date of Patent: Apr. 26, 1994

[54] PROCESS FOR PRODUCING A HUMAN NEUTROPHIL CHEMOTACTIC FACTOR PEPTIDE AND A RECOMBINANT EXPRESSION VECTOR FOR THE SAID POLYPEPTIDE

[75] Inventors: Masaaki Yamada, Kyoto; Ryuji Furuta, Ohtsu; Junichi Yamagishi, Nara, all of Japan; Kouji Matsushima; Teizo Yoshimura, both of Frederick, Md.

[73] Assignee: The United States of America as represented by the Secretary of the Department of Health and Human Services, Washington, D.C.

[21] Appl. No.: 711,275

[22] Filed: Jun. 4, 1991

Related U.S. Application Data

[63] Continuation of Ser. No. 189,164, May 2, 1988, abandoned.

[51] Int. Cl.$^5$ .............. C12P 21/02; C12P 19/34; C12N 15/00; C12N 7/00
[52] U.S. Cl. .............. 435/69.5; 435/172.3; 435/252.33; 435/320.1; 435/235.1; 530/300; 935/10; 935/29; 935/11; 935/56; 935/73
[58] Field of Search .............. 435/69.5, 91, 172.3, 435/252.33, 320.1, 235.1; 536/27; 530/300; 935/10, 29, 11, 56, 73

[56] References Cited

PUBLICATIONS

Pouwels et al Cloning Vectors, A Laboratory Manual Elsevier Press (1985).
Schmid et al J. Immun. vol. 139 pp. 250-256 (1987).
Ikehara et al Proc. Natl. Acad. Sci. USA vol. 81 p. 5956-5960 (1984).
Schulz et al J. Bact. vol. 169 p. 5385-5392 (1987).
Shen Chemical Abstracts vol. 101 (23) p. 151 Abstract No. 205 263 page (1984).
Shen Proc. Natl. Acad. Sci. USA vol. 81 pp. 4627-4631 (1984).
Marstan, Biochem J. vol. 240 pp. 1-12 (1986).
Matsushima et al. J. Exp. Med., vol. 167, Jun. 1988 pp. 1883-1893.
Naofumi et al., The FASEB Journal, vol. 3, No. 3 Feb. 9, 1989 Abstract No. 1615.
Matsushima et al., Biological Abstracts/RRM Abstract No. 36/22061.
Yoshimura et al., Prc. Natl. Acad. Sci. USA, vol. 84 pp. 9233-9237, Dec. 1987.
Matsushima et al. The FASEB Journal, vol. 2 No. 5, Mar. 20, 1988, Abstract No. 6683.

*Primary Examiner*—Joan Ellis
*Attorney, Agent, or Firm*—Wenderoth Lind & Ponack

[57] ABSTRACT

An expression vector in which a DNA encoding a human neutrophil chemotactic factor polypeptide is inserted, a transformant (a host cell transformed with the expression vector), and a process for production of the said polypeptide by using the said transformant.

5 Claims, 5 Drawing Sheets

FIG. 1a

Construction of an expression plasmid pHNP101

Human NCFcDNA clone: pUC19-1.7-5
  ├─digested with PstI and EcoRI
  ↓

PstI-EcoRI-DNA fragment
  ├─cloned into M13mp18 vector
  ├─infected E. coli JM105
  ↓

Recombinant phage
  ├─infected E. coli CJ236
  ├─cultivated in uridine containing medium
  ↓

Uracil containing DNA template
  ├─annealed a mutagenic 33-mer primer [E]
  ↓

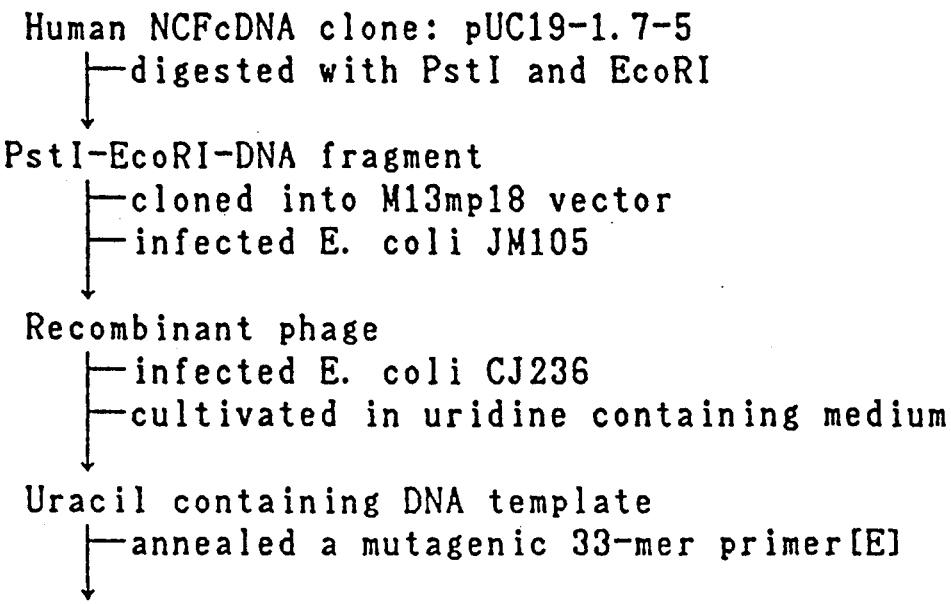

Uracil containing DNA template

├─extended the primer with T4 DNA polymerase
  ├─ligated the ends with T4 DNA ligase
  ↓

Heteroduplex
  ├─transformed E. coli JM105
  ↓

Mutated Double-Stranded DNA
  ├─digested with DraI and EcoRI
  ↓

NCF(DraI-EcoRI)-fragment

FIG. 2a

Construction of an expression vector pEP205

Plasmid pBR322
    ├─digested with AvaI and PvuII
    ↓

Larger DNA(3.7kbp)-fragment
    ├─filled in the cohesive ends to blunt-ends
    │  with DNA polymerase I(Klenow fragment)
    ├─ligated with T4 DNA ligase
    ↓

Plasmid Vector pBRS6
    ├─digested with EcoRI and PstI
    ↓

Amp(PstI-EcoRI)-fragment           pBRS6-larger
    ├─cloned into M13mp18 vector    fragment*
    ├─infected E. coli JM105
    ↓

Recombinant phage
    ├─infected E. coli CJ236
    ├─cultivated in uridine containing medium
    ↓

Uracil containing DNA template
    ├─annealed a mutagenic oligonucleotide primer [G]
    ↓

```
                        G
         CAGAACTTT AAAGTGCTC
    ─GTGTATCGTCTTGAAA TTTCACGAGTAGT─
                        T
```
Uracil containing DNA template ├─extended the primer with T4 DNA polymerase
    ├─ligated the ends with T4 DNA ligase
    ↓

Heteroduplex

PROCESS FOR PRODUCING A HUMAN NEUTROPHIL CHEMOTACTIC FACTOR PEPTIDE AND A RECOMBINANT EXPRESSION VECTOR FOR THE SAID POLYPEPTIDE

This application is a continuation application of now abandoned application, Ser. No. 189,164 filed May 2, 1988.

This invention relates to an expression vector in which a DNA encoding a human neutrophil chemotactic factor polypeptide is inserted, a transformant (a host cell transformed with the expression vector), and a process for production of the said polypeptide by using the said transformant.

Human neturophil chemotactic factor (abbreviated NCF hereinafter) is a physiologically active polypeptide which is produced from human mononuclear leukocytes stimulated with lipopolysaccharide, and has biological activity specifically to attract neutrophils, and is evaluated as one of the modulating factors relating to the initial stage of the inflammatory reaction (Yoshimura, T. et al., J. Immunol., 139, 788, 1987).

On the other hand, neutrophils infiltrate into the foci of bacterial infection, inflammation site and around malignant tumor cells, and play important role in homeostatic defense mechanism. Neutrophils are attracted and further activated by NCF or by the combination of NCF with interleukin-1. For example, the use of the combination of NCF and interleukin-1 are expected a the drug for treatment of certain bacterial infectious diseases or cancers.

As for the said NCF derived from human mononuclear leukocytes, its partial amino acid sequence has already been determined (Yoshimura, T. et al., Proc. Natl. Acad. Sci., USA, 84, 9233, 1987). The present inventors have succeeded in isolation of a cDNA encoding the human NCF based on the above partial amino acid sequence (see Referential Example 1). The base (nucleotide) sequence of the cloned human NCF cDNA was identical in the coding region with the base sequence reported by Schmid and Weissmann (J. Immunol., 139, 250, 1987). A human NCF polypeptide was found to be a polypeptide with the low molecular weight of 8.4 kD since the complete primary structure of its polypeptide was established by the genetic analysis.

As regards various physiologically active polypeptides, such as interleukin-1, interleukin-2, interleukin-3, TNFα (tumor necrosis factor), lymphotoxin (TNFβ), GM-CSF (granulocyte-macrophage colony stimulating factor), G-CSF (granulocyte colony stimulation factor) and various interferons, the production of these polypeptides having the molecular weight of more than 10 kD has been achieved by the use of recombinant DNA technology. But in the case of producing a polypeptide with the low molecular weight by recombinant DNA technology, especially by using $E.$ $coli$ as the host, it is usually produced as a fused protein with the protein derived from $E.$ $coli$ in general, in order to avoid degradation in the host cells. For example, Schulz et al. reported that it is extremely difficult to produce directly a human somatomedin C polypeptide (7.7 kD) consisting of 69 amino acid residues by recombinant DNA technology using $E.$ $coli$ as the host, and they succeeded in the efficient production of it as a dimer polypeptide or the truncated derivatives of the dimer polypeptide by recombinant DNA technology in $E.$ $coli$ (Schulz, M-F. et al., J. Bacteriol., 169, 5385, 1987). The degree of this degradation is closely related to the structure of the polypeptide, and this relationship is more likely when the molecular weight of the required polypeptide is lower, and particularly, most likely in the case of an extremely lower molecular weight polypeptide in $E.$ $coli$ (Itakura, K. et al., Science 198, 1056, 1977).

The present inventors attempted to express directly the human NCF polypeptide with such lower molecular weight by applying recombinant DNA technology using $E.$ $coli$ as the host. Consequently, it has been found unexpectedly that the said polypeptide could be produced efficiently without significant degradation in the host cells.

The object of this invention is to offer an efficient process for the production of a human NCF polypeptide by recombinant DNA technology.

Another object of this invention is to offer a recombinant expression vector in which a DNA encoding a human NCF polypeptide is inserted and a host cell transformed with the said vector.

Other objects will be understood from the following description.

According to this invention, a human NCF polypeptide, particularly, a polypeptide consisting of an amino acid sequence represented by formula [I] shown in Table 1, can be produced by applying recombinant DNA technology in microorganisms or animal cells.

TABLE 1 formula [I]

SerAlaLysGluLeuArgCysGlnCysIleLysThr

TyrSerLysProPheHisProLysPheIleLysGlu

LeuArgValIleGluSerGlyProHisCysAlaAsn

ThrGluIleIleValLysLeuSerAspGlyArgGlu

LeuCysLeuAspProLysGluAsnTrpValGlnArg

ValValGluLysPheLeuLysArgAlaGluAsnSer

As a base sequence of a DNA encoding a polypeptide consisting of an amino acid sequence represented by formula of [I], the DNA consisting of a base sequence represented by formula [A] shown in Table 2 and its degenerative sequence are illustrated.

TABLE 2 formula [A]

5'-AGTGCTAAAGAACTTAGATGTCAGTGCATAAAGACA

TACTCCAAACCTTTCCACCCCAAATTTATCAAAGAA

CTGAGAGTGATTGAGAGTGGACCACACTGCGCCAAC

ACAGAAATTATTGTAAAGCTTTCTGATGGAAGAGAG

CTCTGTCTGGACCCCAAGGAAAACTGGGTGCAGAGG

GTTGTGGAGAAGTTTTTGAAGAGGGCTGAGAATTCA-3'

The DNA encoding a human NCF polypeptide can be isolated, for example, according to the method as described in Referential Example 1 and the method reported by Schmid and Weissmann as mentioned above. It is also possible to perform the total synthesis of the said DNA chemically. As regards the extra region or deficient region of the resulting DNA, the required DNA can be produced by the methods of digestion and/or repairment such as, for example, digesting by an appropriate restriction enzyme and ligating with chemically synthesized oligodeoxy-ribonucleotides.

By adding a translation initiation codon ATG to the 5'-terminus (upstream) of this DNA, ligating a DNA fragment containing a termination codon to the 3'-terminus (downstream) of the DNA having the initiation codon, connecting the resulting DNA with a proper promoter (e.g. trp, lac, phoS, PL, SV40 early promoter) and SD sequence, and then inserting the resulting DNA having the proper promoter and SD sequence into a proper vector (e.g. plasmid pBR322), an expression vector for production of the human NCF polypeptide is constructed.

The base sequence from the SD sequence to the translation initiation codon is preferably represented by formula [D].

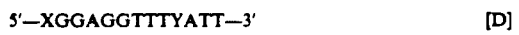

5'—XGGAGGTTTYATT—3'    [D]

wherein X means (A)x, wherein A is adenine and x is 1 to 5, and Y means (A)y(T)z, wherein A is adenine, T is thymine, y is 0 to 3, and z is 0 or 1.

A transformant of this invention can be obtained by introducing the expression vector constructed as above into a proper host cell, for example *E. coli* according to the method of Cohen et al. (Cohen, S. N., et al., Proc. Natl. Acad. Sci., USA, 69, 2110, 1972).

The human NCF polypeptide can be produced by cultivating the transformant of this invention under suitable culture conditions. The extract containing the said polypeptide can be obtained from the culture after destroying the cells, for example by lysozyme digestion and freeze-thawing, sonication or by using a French press, followed by collecting the extract by centrifugation or filtration.

The human NCF polypeptide can be purified from the extract by purification methods characterized by combination of treatment for removing nucleic acids, salting-out, anion and/or cation exchange chromatography, ultrafiltration, gel filtration, if necessary, dialysis, electrophoresis, affinity chromatography using specific antibodies, and so on.

The chemical, physicochemical and biological properties of the human NCF polypeptide will be described hereinafter in detail.

The highly purified human NCF polypeptide obtained in the Example (to be referred to as the recombinant human NCF) was used for analyses as shown below.

(1) Molecular weight

Molecular weight of the recombinant human NCF was measured by SDS-polyacrylamide gel electrophoretic analysis. As molecular weight marker proteins, the standard protein kit (Pharmacia Fine Chemicals, Sweden) consisting of the following proteins was used: lysozyme (14.4 kD), soybean trypsin inhibitor (20.1 kD), carbonic anhydrase (30 kD), ovalbumin (43 kD), bovine serum albumin (67 kD) and phosphorylase b (94 kD).

As a result, the recombinant human NCF had a molecular weight of approximately 8~10 kD.

Polymerized molecule of the recombinant human NCF due to the formation of intermolecular disulfide bond was not detected significantly.

(2) Amino acid sequence

The amino acid sequences of the recombinant human NCF were determined by the Automated Edman degradation method.

The recombinant human NCF was previously treated by reductive cleavage of disulfide bonds with 2-mercaptoethanol, followed by S-β-4-pyridylethylation of cysteine residues with 4-vinyl pyridine according to the method of Fullmer (Anal. Biochem., 142, 336, 1984).

Separately, several kinds of peptide fragments of the recombinant human NCF were prepared and isolated according to the following methods.

The recombinant human NCF was treated with 70% formic acid by the method of Sonderegger et al. (Anal. Biochem., 122, 298, 1982) to cleave specifically Asp-Pro peptide bond. From the resulting two peptide fragments, the C-terminal fragment was isolated by high-performance liquid chromatography using a column of SynChropak RP-P (SynChrom, Inc., USA) under the elution condition of a linear gradient of acetonitrile concentric from 0 to 50% in 0.1% trifluoroacetic acid.

The pyridylethylated human NCF was digested with a metalloendopeptidase (EC 3.4.24; Seikagaku Kogyo, Japan) and the resulting peptide fragments were isolated by high-performance liquid chromatography under the elution condition of a linear gradient of acetonitrile concentration from 0 to 30% in 0.1% trifluoroacetic acid.

N-terminal amino acid sequences of the pyridylethylated NCF and each peptide fragment were determined with a Protein Sequencer, Model 470A (Applied Biosystems, USA) and a SP8440 UV/VIS detector (Spectra-Physics, USA).

It was found that the N-terminal amino aid sequence of the pyridylethylated recombinant human NCF was as follows:

SerAlaLysGluLeuArgCysGlnCysIleLysThrTyrSer

LysProPheHisProLysPheIleLysGluLeuArgValIle

GluSerGlyProHisCysAlaAsn

This amino acid sequence was completely identical with the amino acid sequence from N-terminal Ser to Asn at the 36th position of the human NCF polypeptide represented by formula [I] shown in Table 1. A methionine residue due to the translation initiation codon (AG) could not be detected at the N-terminus.

It was also found that the N-terminal amino acid sequence of the acid-cleavaged C-terminal fragment was as follows:

ProLysGluAsnTrpValGlnArgValValGluLys-
PheLeu LysArgAlaGluAsnSer

This amino acid sequence was identical with the amino acid sequence from the 53rd position from the N-terminus to the C-terminal Ser of the human NCF polypeptide represented by formula [I] shown in Table 1.

The amino acid sequences of the two peptide fragments prepared by digestion with metalloendopeptidase were determined as follows:

LysGluLeuArgValIleGluSerGlyProHisCysAlaAsn
ThrGluIleIleVal and

LysLeuSerAspGlyArgGluLeuCysLeuAspPro

These amino acid sequences were identical with the amino acid sequence of 19 residues from the 23rd position to the 41st position from the N-terminus and the amino acid sequence of 12 residues from the 42nd position to the 53rd position from the N-terminus of the human NCF polypeptide represented by formula [I] shown in Table 1.

Consequently, it has been confirmed that the amino acid sequence of the recombinant human NCF polypeptide is completely identical with the sequence deduced from a base sequence encoding the human NCF.

(3) Extinction coefficient

The recombinant human NCF polypeptide was lyophilized without any carrier component. Contents of water and ash in this lyophilized product were determined to be 6.01% and 0.52%, respectively.

Extinction coefficient value of the recombinant human NCF was calculated to be 8.25 at 280 nm under the conditions of 1% aqueous solution and 1 cm optical path length.

(4) Chemotactic activity

Neutrophil chemotactic activity was measured in a multiwell chemotaxis Boyden chamber (Neuro Probe, Inc., USA) as reported by Harvath, L. et al. (J. Immunol. Methods, 37, 39, 1980). Recombinant NCF was serially diluted in Dulbecco's Modified Eagle's Medium (DMEM) supplemented with 1% bovine serum albumin (BSA). Normal human neutrophils were purified from Buffy coat collected from healthy donors (National Institutes of Health, Blood Bank, USA) by separating on Ficoll-Hypaque followed by lysing contaminating red blood cells with ACK-lysing buffer. The purity of neutrophils were more than 95% by staining cells with Giemsa solution. The viability was also more than 95% as judged by a trypan blue dye exclusion test. The neutrophil cells were incubated at a cell density of one million cells/ml in DMEM supplemented with 1% BAS for 40 minutes at 37° C. The migrated neutrophils which adhered onto a membrane (3 μm: Nuclepore Corp., USA) were fixed with methanol and stained with Giemsa solution. At 0.1 n g/ml significant migration was observed by examining with microscope. At 10 n g/ml maximal migration was observed. The migrated cells were identified to be neutrophils morphologically.

For simplification of the description, the following abbreviations are used in the present specification and claims.

A: adenine
C: cytosine
G: guanine
T: thymine
I: Inosine
dATP: deoxyadenosine triphosphate
dCTP: deoxycytidine triphosphate
dGTP: deoxyguanosine triphosphate
dTTP: deoxythymidine triphosphate
ATP: adenosine triphosphate
DNA: deoxyribonucleic acid
cDNA: complementary DNA
kbp: kilobase pairs
SD sequence: Shine-Dalgarno sequence
kD: kilodaltons SDS: sodium laurylsulfate
[3H]-thymidine: tritiated thymidine In the present specification and claims, the nucleotide sequence shown by a single strand is the nucleotide sequence of a sense strands, and the left end is a 5'-terminus and the right end is a 3'-terminus. In the amino acid sequence, the left end is an N-terminus, and the right end is a C-terminus.

The following Example and Referential Examples illustrate this invention more specifically.

It should be understood however that the invention is in no way limited to these examples.

For a better understanding of the following Example and Referential Examples, FIGS. 1 to 3 are attached to the present specification.

EXAMPLE

Production of Human NCF Polypeptide

Figure 1B:
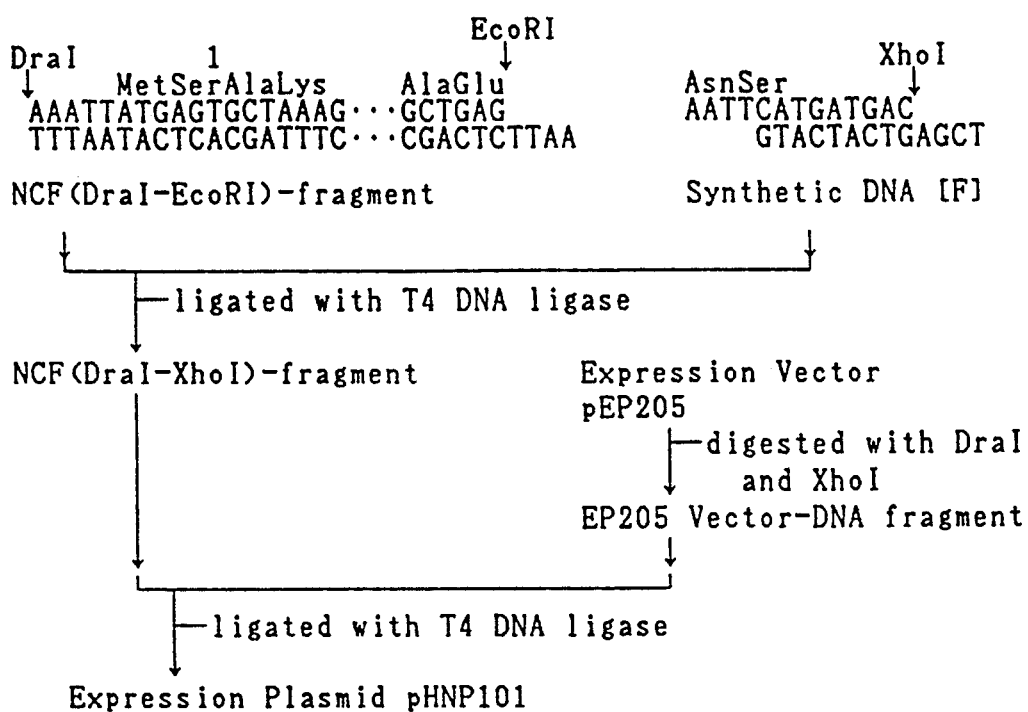
FIG. 1 shows a process of constructing an expression plasmid pHNP101 (Example)

Human NCF polypeptide having an amino acid sequence represented by formula[I] in Table 1, was produced by the following methods.

(1) Construction of an expression plasmid pHNP101

From the recombinant plasmid pUC19-1.7-5 in which human NCFcDNA was inserted as mentioned in Referential Example 1, DNA fragment encoding the polypeptide corresponding to the amino acids from the 18th position to the 97th position from the N-terminus of human NCF precursor polypeptide (corresponding to the base sequence from the base No. 52 to No. 291 in Table 3) was isolated by digestion with restriction endonucleases PstI and EcoRI. This DNA fragment was then cloned into a phage vector M13mp18 (Takara Shuzo Co., Japan) at a region between the restriction endonuclease cleavage site of PstI and that of EcoRI in the polylinker sequence. By using the resultant recombinant phage DNA, the specific base sequence being 5'—TTTAAATTATG—3' was inserted between the codon corresponding to Arg at the 27th position from N-terminus of the human NCF precursor polypeptide and the codon corresponding to Ser at the 28th position, by the technique of site-directed mutagenesis according to the method of Kunkel et al. (Methods in Enzymol., 154, 367-382, 1987). The site-directed mutagenesis was carried out using a Muta-Gene in vitro mutanegesis kit according to the instruction manual (Bio-Rad Labs., USA).

E. coli JM105 was infected with the recombinant phage DNA, and then it was cultivated to collect the recombinant phage. Then, E. coli CJ236 was infected with the recombinant phage obtained as above and cultivated in 2xTY medium [composition; 1.6% tryptone, 1% yeast extract, 0.5% sodium chloride] supplemented with uridine (1 μg/ml) and chloramphenicol (20 μg/ml) at 37° C. for 5 hours. The single-stranded phage DNA containing uracils was isolated from the culture medium.

Separately, a mutagenic oligodeoxyribonucleotide primer consisting of 33 bases represented by the following formula [E] was chemically synthesized.

5'—GTTTTGCCAAGGTTTAAATTAT-GAGTGCTAAG—3'   formula [E]

The 5'-end of the mutagenic primer was previously phosphorylated. The phosphorylated primer was annealed with the single-stranded phage DNA containing uracils prepared as above in an annealing buffer [20 mM Tris-HCl buffer (pH 7.4) containing 2 mM magnesium chloride and 50 mM sodium chloride] by incubating at 70° C. for 10 minutes, followed by cooling down to 30° C. at a rate of 1° C. per minute. Then, the primer was extended with T4 DNA polymerase in a synthesis buffer [10 mM Tris-HCl buffer (pH 7.4) containing 0.4 mM deoxynucleoside triphosphate (dGTP, dATP, dCTP, dTTP), 0.75 mM ATP, 3.75 mM magnesium chloride and 1.5 mM dithiothreitol] to synthesize a complementary strand and the ends were ligated with T4 DNA ligase by sequential incubating on ice for 5 minutes, at least 25° C. for 5 minutes and at 37° C. for 90 minutes. The reaction was stopped by freezing at −20° C. The circular double-stranded DNA (heteroduplex) was introduced into E. coli JM105 cells, and they were cultivated to isolate the mutated double-stranded replicative form DNA. The nucleotide sequence of the mutated DNA was confirmed by sequencing the single-stranded DNA isolated from the culture medium.

The resultant mutated double-stranded DNA was digested with restriction endonucleases DraI and EcORI in order to isolate a DNA fragment containing most of the encoding region for human NCF polypeptide. The isolated DNA fragment is, hereinafter, referred to as the NCF(DraI-EcORI)-fragment.

This NCF(DraI-EcORI)-fragment was ligated by T4 DNA ligase with a chemically synthesized oligodexoynucleotide adaptor represented by the following formula [F].

formula [F]

The resultant ligated DNA fragment is referred to as the NCF(DraI-XhoI)-fragment.

Separately, an expression plasmid pEP205 as mentioned in Referential Example 2 was digested with restriction endonucleases DraI and XhoI, and the resulting larger DNA fragment including an ampicillin-resistance gene and a replication origin (hereinafter referred to as the EP205 vector-DNA fragment) was isolated, and this EP205 vector-DNA fragment was ligated by T4 DNA ligase with the NCF(DraI-XhoI)-fragment previously prepared in order to construct an expression plasmid pHNP101 for producing human NCF (see FIG. 1).

(2) Transformation of Escherichia coli

The resulting expression plasmid pHNP101 was introduced into E. coli HB101 by the following manner.

E. coli HB101 was inoculated in the LB broth [composition; 1% tryptone, 0.5% yeast extract, 1% sodium chloride (pH 7.5)], and cultivated overnight at 30° C. One milliliter of the resulting culture was inoculated in 100 ml of LB broth and further cultivated at 30° C. until the turbidity at 600 nm of the culture reached approximately 0.6. After standing for 30 minutes in ice water, the cells were collected by centrifugation. They were resuspended in 50 ml of 50 mM calcium chloride, and allowed to stand for 60 minutes in ice water. Then, the cells were collected by centrifugation and again suspended in 10 ml of 50 mM calcium chloride containing 20% glycerol.

To this cell suspension, the expression plasmid pHNP101 was mixed and incubated sequentially in ice water for 20 minutes and at room temperature for 60 minutes. Then, the LB broth was added to the cell suspension, and it was cultivated under shaking at 37° C. for 60 minutes. An aliquot of the resulting cell suspension was seeded on the LB agar (1.5% agar) plates containing 25 μg/ml of ampicillin. After cultivation at 37° C. overnight, ampicillin-resistant colonies were selected to obtain transformants. One of the transformants was named E. coli HB101/pHNP101 and it was used for production of the human NCF polypeptide.

(3) Production of human NCF polypeptide

E. coli HB101/pHNP101 obtained in section (2) was cultivated in the LB broth overnight at 37° C. The culture was inoculated in 100-fold volumes of the nutrient medium [composition; 1.5% sodium phosphate, dibasic 12-water, 0.3% potassium phosphate, monobasic, 0.1% ammonium chloride, 2 mg/liter vitamine B1, 0.5% casamino acid, 2 mM magnesium sulfate, 0.1 mM calcium chloride, 1% tryptone, 0.5% yeast extract, 1% sodium chloride and 0.4% glycerol] and then, 3-indoleacrylic acid was added to give a final concentration of 20 μg/ml. The cultivation was done at 35° C. for 28 hours. The cells were collected by centrifugation, and suspended in 50 mM Tris-Hcl buffer (pH 8.0) continuing 0.1% lysozyme and 30 mM sodium chloride. The suspension was allowed to stand in ice water for 30 minutes. Further, freezing in a dry ice/ethanol bath and thawing at 37° C. were repeated to disrupt the cells. After adding 1/50 volume of 10% ethyleneimine polymer, a clarified cell-extract was obtained by centrifugation. To this cell-extract ammonium sulfate was added to give a 70% saturation, and the formed precipitate was collected by centrifugation. The precipitate was dissolved in distilled water and it was dialyzed against 5 mM phosphate buffered saline (pH 6.5) (hereinafter referred to as PBS). The dialysate was applied onto a column of Sephacryl S-200 (Pharmacia, Sweden), and the fractions containing polypeptides having about 6 to 10 kD molecular weight were collected and pooled. The molecular sizes of polypeptides in each eluate were measured by SDS-polyacylamide gel electrophoretic analysis. The pooled fraction was dialyzed against 20 mM phosphate buffer (pH 6.5) (hereinafter referred to as PB). Then, the dialysate was applied onto a column of CM-Sepharose CL-6B (Pharmacia, Sweden) previously equilibrated with PB. The column was washed with PB, and eluted with a linear gradient of sodium chloride molarity from 0 to 0.5M in PB. The fractions containing the human NCF polypeptide were collected and pooled, and concentrated by ultrafiltration. Further, the concentrate was subjected to gel filtration on Toyopearl HW-55 column (TOSOH Co., Japan) to obtain the highly purified human NCF polypeptide.

By SDS-polyacrylamide gel electrophoretic analysis, any impurity was not detected in the highly purified human NCF polypeptide preparation.

This human NCF preparation was used for chemical, physicochemical and biological analyses as shown previously.

REFERENTIAL EXAMPLE 1

Cloning of cDNA Encoding Human NCF

The cDNA library was constructed by insertion of cDNA synthesized from normal human monocyte polyadenylated mRNA obtained from the monocyte stimulated with 10 μg/ml lipopolysaccharide for 6 hurs, into the EcoRI site of the phage vector λgt10. One half million individual plaques were screened for hybridization with [32P]-labeled two kinds of chemically synthesized oligonucleotide probes represented by the following formulae:

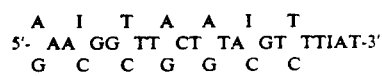

-continued and

```
           A   I   T   I   A   I   T
5'- AA  GG  TT  GA  TA  GT  TTIAT-3'
           G   C   C   G   C   C
```

In the first screening, 13 putative positive clones were obtained. From these positive clones, one clone (termed r-MDNCF 2-1) was selected in the second screening by using the another probe. The phage DNA in r-MDNCF 2-1was subcloned into the pUC19 plasmid.

The resulting recombinant plasmid was termed pUC-19-1.7-5. The cloned cDNA in a recombinant plasmid pUC19-1.7-5 contains a nucleotide sequence encoding human NCF shown in Table 3.

REFERENTIAL EXAMPLE 2

Construction of an Expression Vector pEP205

Plasmid pBR322 was digested with restriction endonucleases AvaI and PvuII, and the resulting larger DNA fragment (about 3.7 kbp in size) was isolated. After filling-in its cohesive ends to blunt-ends with *E. coli* DNA polymerase I (Klenow fragment) in the presence of dGTP, dATP, dCTP and dTTP, both ends were ligated by T4 DNA ligase to construct a new plasmid vector (designated pBRS6), which was deleted a copy number regulatory gene region located near the replication origin of the plasmid pBR322.

The plasmid vector pBRS6 was digested with restriction endonucleases EcoRI and PstI, and a smaller DNA fragment containing an upstream region of the ampicillin-resistance gene (about 0.75 kbp in size) was isolated. The resultant DNA fragment is referred to as the Amp(PstI-EcoRI)-fragment.

This Amp(PstI-EcoRI)-fragment was cloned in a phage vector M13mp18 as mentioned in the Example. By using the resultant recombinant phage DNA, one base (T) in the nucleotide sequence of the Amp(PstI-EcoRI)-fragment was changed to another base (C) by the site-directed mutagenesis according to the method as mentioned in the Example, in order to eliminate the specific nucleotide sequence (AAATTT) recognizable with the restriction endonuclease DraI.

The single-stranded phage DNA containing uracils was isolated from the culture medium of *E. coli* CJ236 infected with the above recombinant phage DNA. As a mutagenic primer, the oligodeoxyribonucleotide represented by the following formula [G] was chemically synthesized.

5'—CAGAACTTTGAAAGTGCTC—3'    [G]

The phosphorylated primer was annealed with the uracil-containing DNA template. According to the method described in Example section (1), the desired mutated double-stranded DNA was isolated.

The resultant mutated double-stranded DNA was digested with restriction endonucleases PstI and EcoRI in order to isolate a DNA fragment corresponding to the Amp(PstI-EcoRI)-fragment as mentioned above, but not containing the restriction endonuclease DraI cleavage recognition sequence [hereinafter referred to as the mutated Amp(PstI-EcoRI)-fragment]. The mutated Amp(PstI-EcoRI)-fragment was ligated with the larger DNA fragment isolated from the vector pBRS6 by digestion with restriction endonucleases EcoRI and PstI, in order to construct a new vector which was eliminated the DraI cleavage recognition sequence in the ampicillin resistance gene of the plasmid vector pBRS6. This new vector is designated pBRS601.

Further, the is new vector pBRS601 was digested with restriction endonuclease DraI, and the resulting larger DNA fragment was isolated. The larger DNA fragment was ligated with SmaI linker (Takara Shuzo Co., Japan) by T4 DNA ligase to construct a new plasmid vector. This resulting new plasmid vector is a derivative of plasmid pBRS6 and is not containing nay recognition sequences for the restriction endonuclease DraI. This new plasmid vector is designated pBRS602.

The nucleotide sequence of the SmaI linker is shown below.

5'—CCCGGG—3'

Furthermore, this new vector pBRS602 was digested with restriction endonuclease AatII and SalI, and the resulting larger DNA fragment was isolated [hereinafter referred to as the BRS602 (AatII-SalI)-fragment].

Separately, an expression plasmid pHIPH383a for producing human interleukin-1α as mentioned in Referential Example 3, was digested with restriction endonucleases AatII and SalI, and the resulting DNA fragment containing *E. coli* tryptophan promoter sequence and the coding region for human interleukin-1α was isolated. This resulting DNA fragment is referred to as the trp promoter/IL1α-DNA fragment.

Figure 2B:
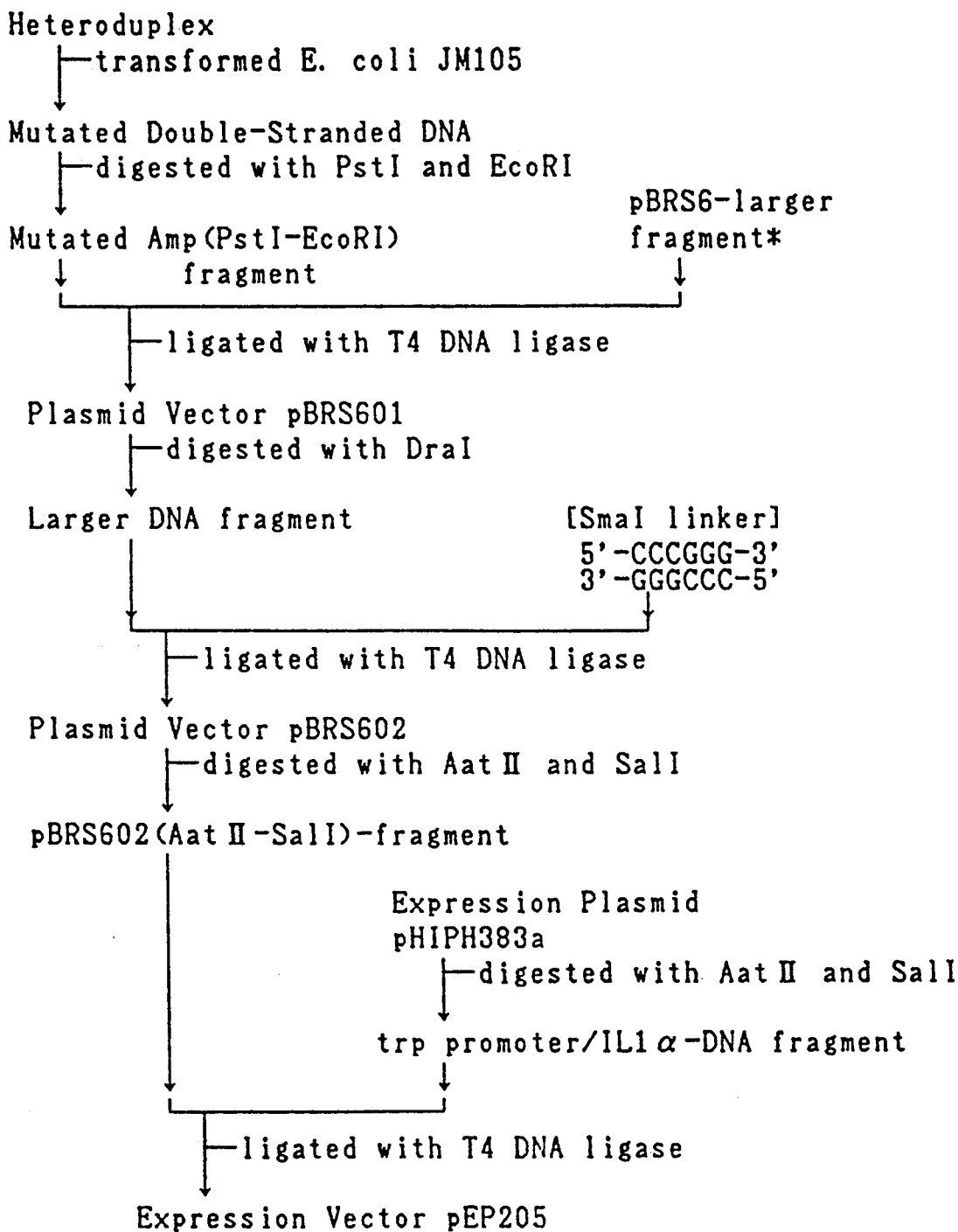
FIG. 2 shows a process of constructing an expression vector pEP205 (Referential Example 2)

This trp promoter/IL1α-DNA fragment was ligated with the pBRS602 (AatII-SalI)-fragment by T4 DNA ligase to construct a new expression plasmid (see FIG. 2).

This new expression plasmid is designated pEP205.

REFERENTIAL EXAMPLE 3

Construction of an Expression Plasmid pHIPH383a

The cloned cDNA encoding human interleukin-1α precursor polypeptide was isolated according to the method described in European Patent Publication No. 0188920.

From the recombinant plasmid pHL4 containing human interleukin-1α precursor cDNA (Furutani, Y., et al., Nucleic Acids Res., 13, 5869, 1985), the cDNA insert was isolated by digestion with restriction endonuclease PstI, and further digested with restriction endonucleases EcoRI and BstNI, to isolate a DNA fragment (411 bp in size) containing a middle portion of the coding region for the mature human interleukin-1α. The isolated DNA fragment corresponds to the nucleotide sequence from base No. 398 to No. 808 in Table 6 shown in European Patent Publication No. 0188920.

This DNA fragment was sequentially ligated by T4 DNA ligase with chemically synthesized oligodeoxyribonucleotide adaptors represented by the following formulae [H] and [I]. The resulting DNA fragment is referred to as the SD-IL1-fragment.

The synthetic oligodeoxyribonucleotide adaptor [H] was prepared by sequential ligation of the following five kinds of DNA fragments represented by formulae [a]'[e].

```
5'-AACTAGTACGCAAGTTCAC          [a]
3'-TTGATCATGCGTTCAAGTGCATT

5'-GTAAAAGGAGGTTTAAA            [b]
  3'-TTCCTCCAAATTTAATAC
```

```
5'-TTATGTCATCACCTTTTAG                              [c]
   3'-AGTAGTGGAAAATCGAAGG

[d]
5'-CTTCCTGAGCAATGTGAAATACAACTTTA
   3'-ACTCGTTACACTTTATGTTGAAATACTC
``` and

```
5'-TGAGGATCATCAAATACG                               [e]
   3'-CTAGTAGTTTATGCTTAA
```

The base sequence of the formula [I] was as follows;

```
5'-AGGCGTGATGACTCGA                           formula [I]
   3'-CCGCACTACTGAGCTCTAG
```

Separately, an expression vector pEP302 (Furutani, Y., et al., Nucleic Acids Res. 13, 5869, 1985) was digested with restriction endonucleases HpaI and BamHI, and the resulting larger DNA fragment containing *E. coli* tryptophan promoter sequence and an ampicillin resistance gene, was isolated (hereinafter referred to as the EP302 vector-DNA fragment).

Figure 3:
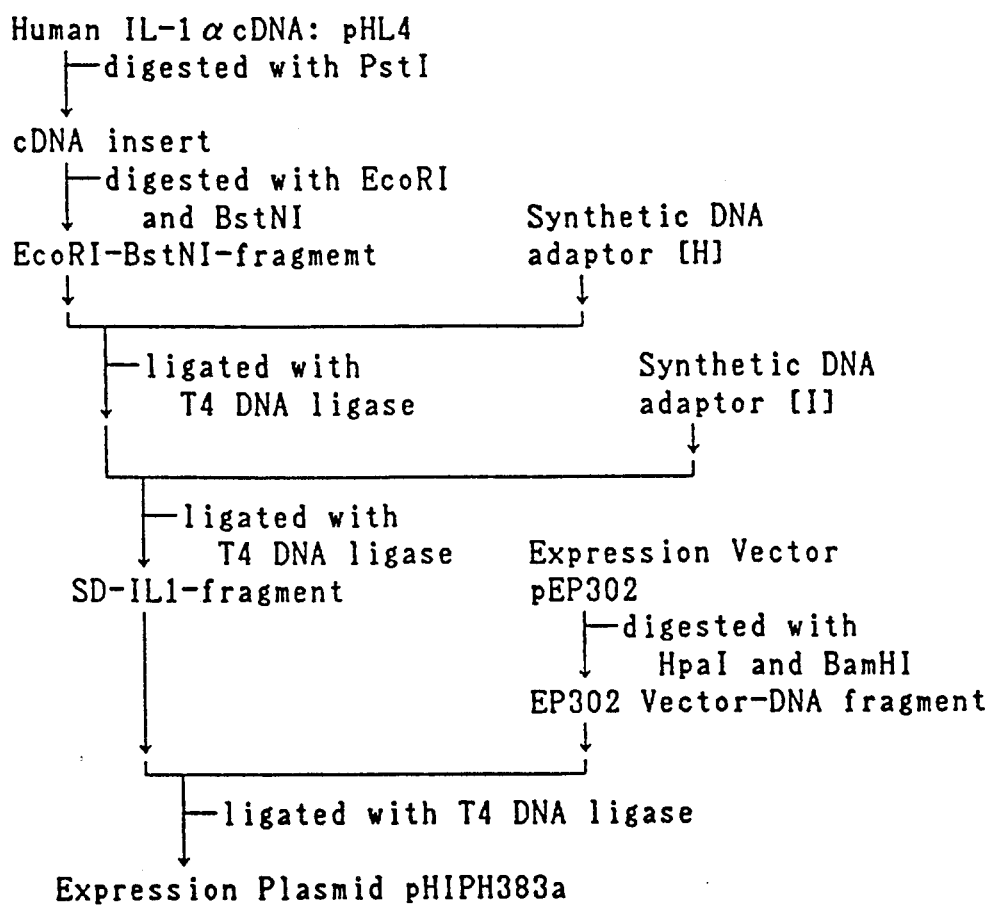
FIG. 3 shows a process of constructing an expression plasmid pHIPH383a (Referential Example 3).

The EP302 vector-DNA fragment was ligated by T4 DNA ligase with the SD-IL1-fragment prepared as above to construct an expression plasmid pHIPH383a for producing the mature human interleukin-1α polypeptide (see FIG. 3).

TABLE 3

| Nucleotide Sequence of Human NCF Precursor cDNA and Its Deduced Amino Acid Sequence | | |
|---|---|---|
| Met Thr Ser Lys Leu Ala Val Ala Leu Leu | 10 | |
| ATGACTTCCAAGCTG GCCGTGGCTCTCTTG | 30 | |
| Ala Ala Phe Leu Ile Ser Ala Ala Leu Cys | 20 | |
| GCAGCCTTCCTGATT TCTGCAGCTCTGTGT | 60 | |
| Glu Gly Ala Val Leu Pro Arg Ser Ala Lys | 30 | |
| GAAGGTGCAGTTTTG CCAAGGAGTGCTAAA | 90 | |
| Glu Leu Arg Cys Gln Cys Ile Lys Thr Tyr | 40 | |
| GAACTTAGATGTCAG TGCATAAAGACATAC | 120 | |
| Ser Lys Pro Phe His Pro Lys Phe Ile Lys | 50 | |
| TCCAAACCTTTCCAC CCCAAATTTATCAAA | 150 | |
| Glu Leu Arg Val Ile Glu Ser Gly Pro His | 60 | |
| GAACTGAGAGTGATT GAGAGTGGACCACAC | 180 | |
| Cys Ala Asn Thr Glu Ile Ile Val Lys Leu | 70 | |
| TGCGCCAACACAGAA ATTATTGTAAAGCTT | 210 | |
| Ser Asp Gly Arg Glu Leu Cys Leu Asp Pro | 80 | |
| TCTGATGGAAGAGAG CTCTGTCTGGACCCC | 240 | |
| Lys Glu Asn Trp Val Gln Arg Val Val Glu | 90 | |
| AAGGAAAACTGGGTG CAGAGGGTTGTGGAG | 270 | |
| Lys Phe Leu Lys Arg Ala Glu Asn Ser | 99 | |
| AAGTTTTTGAAGAGG GCTGAGAATTCA | 297 | |

What is claimed is:

1. A process for producing a human neutrophil chemotactic factor polypeptide consisting of an amino acid sequence of formula [I]:

formula [I]

SerAlaLysGluLeuArgCysGlnCysIleLysThr

TyrSerLysProPheHisProLysPheIleLysGlu

LeuArgValIleGluSerGlyProHisCysAlaAsn

ThrGluIleIleValLysLeuSerAspGlyArgGlu

LeuCysLeuAspProLysGluAsnTrpValGlnArg

ValValGluLysPheLeuLysArgAlaGluAsnSer which comprises directly expressing a nucleotide sequence encoding said polypeptide consisting of the amino acid sequence of the formula [I] in *Escherichia coli* transformed with an expression vector inclusive of said nucleotide sequence.

2. A process according to claim 1, wherein the nucleotide sequence encoding the human neutrophil chemotactic factor polypeptide is a nucleotide sequence of formula [A]:

formula [A]

5'-AGTGCTAAAGAACTTAGATGTCAGTGCATAAAGACA

TACTCCAAACCTTTCCACCCCAAATTTATCAAAGAA

CTGAGAGTGATTGAGAGTGGACCACACTGCGCCAAC

ACAGAAATTATTGTAAAGCTTTCTGATGGAAGAGAG

CTCTGTCTGGACCCCAAGGAAAACTGGGTGCAGAGG

GTTGTGGAGAAGTTTTTGAAGAGGGCTGAGAATTCA-3'.

3. A process for producing a human neutrophil chemotactic factor polypeptide consisting of an amino acid sequence of formula [I]:

formula [I]

SerAlaLysGluLeuArgCysGlnCysIleLysThr

TyrSerLysProPheHisProLysPheIleLysGlu

LeuArgValIleGluSerGlyProHisCysAlaAsn

ThrGluIleIleValLysLeuSerAspGlyArgGlu

LeuCysLeuAspProLysGluAsnTrpValGlnArg

ValValGluLysPheLeuLysArgAlaGluAsnSer which comprises directly expressing the following nucleotide sequence

5'-XGGAGGTTTYATTATG

AGTGCTAAAGAACTTAGATGTCAGTGCATAAAGACA

TACTCCAAACCTTTCCACCCCAAATTTATCAAAGAA

CTGAGAGTGATTGAGAGTGGACCACACTGCGCCAAC

ACAGAAATTATTGTAAAGCTTTCTGATGGAAGAGAG

CTCTGTCTGGACCCCAAGGAAAACTGGGTGCAGAGG

GTTGTGGAGAAGTTTTTGAAGAGGGCTGAGAATTCA-3' wherein X is (A)x, wherein x is 1 to 5, and Y is (A)y(T)z, wherein y is 0 to 3 and z is 0 or 1, in *Escherichia coli* transformed with an expression vector for producing said human neutrophil chemotactic factor polypeptide.

4. A process according to claim 3, wherein x is 4, y is 2 and z is 0.

5. A process according to claim 4, wherein the expression vector is the recombinant plasmid pHNP101.

* * * * *